United States Patent [19]

Cartmell et al.

[11] Patent Number: 4,685,467

[45] Date of Patent: Aug. 11, 1987

[54] X-RAY TRANSPARENT MEDICAL ELECTRODES AND LEAD WIRES AND ASSEMBLIES THEREOF

[75] Inventors: James V. Cartmell; Michael J. Allaire; Larry R. Burcham; Charles T. Patrick, Jr., all of Dayton, Ohio

[73] Assignee: American Hospital Supply Corporation, Evanston, Ill.

[21] Appl. No.: 753,411

[22] Filed: Jul. 10, 1985

[51] Int. Cl.[4] ............................................. A61B 5/04
[52] U.S. Cl. ................................... 128/640; 128/641
[58] Field of Search ............... 128/639, 640, 641, 643; 339/D3, 59, 61

[56] References Cited

U.S. PATENT DOCUMENTS

| | | | |
|---|---|---|---|
| 3,153,561 | 10/1964 | Cooney | 339/61 R |
| 3,406,126 | 10/1968 | Litant . | |
| 3,512,183 | 5/1970 | Sharp et al. . | |
| 3,547,105 | 12/1970 | Ramme . | |
| 3,566,860 | 3/1971 | Moe, Jr. | 128/641 |
| 3,599,629 | 8/1971 | Gordy | 128/640 |
| 3,606,881 | 5/1971 | Woodson | 128/641 |
| 3,828,766 | 8/1974 | Krasnow | 128/641 |
| 3,829,826 | 8/1974 | Brown et al. . | |
| 3,882,853 | 5/1975 | Gofman et al. | 128/641 |
| 3,946,730 | 3/1976 | Monter | 128/641 |
| 3,964,469 | 6/1976 | Manley | 128/641 |
| 3,976,055 | 8/1976 | Monter et al. | 128/643 |
| 4,026,278 | 5/1977 | Ricketts et al. | 128/644 |
| 4,050,453 | 9/1977 | Castillo et al. | 128/640 |
| 4,094,571 | 6/1978 | Benjamin . | |
| 4,102,331 | 7/1978 | Grayzel et al. | 128/640 |
| 4,109,648 | 8/1978 | Larke et al. | 128/639 |
| 4,166,453 | 9/1979 | McClelland | 128/639 |
| 4,237,886 | 12/1980 | Sakurada et al. | 128/303.13 |
| 4,257,424 | 3/1981 | Cartmell | 128/641 |
| 4,268,101 | 5/1981 | Stone | 339/D3 |
| 4,273,135 | 6/1981 | Larimore et al. | 128/640 |
| 4,282,878 | 8/1981 | Novello | 128/641 |
| 4,301,040 | 11/1981 | Berbeco . | |
| 4,332,257 | 6/1982 | Ayer . | |
| 4,353,372 | 10/1982 | Ayer | 128/640 |
| 4,365,634 | 12/1982 | Bare et al. . | |
| 4,369,423 | 1/1983 | Holtzberg . | |
| 4,370,984 | 2/1983 | Cartmell | 128/640 |
| 4,442,315 | 4/1984 | Segawa | 174/36 |
| 4,505,973 | 3/1985 | Neet et al. . | |
| 4,637,672 | 1/1987 | Peterman et al. | 339/61 R |

FOREIGN PATENT DOCUMENTS 1219017  1/1971  United Kingdom .

OTHER PUBLICATIONS

Announcement "ECG Lead Wires are Radiolucent" From Article Spotlight on Electrodes, p. 41 of *Applied Cardiology*, Mar./Apr. 1985.

*Primary Examiner*—Edward M. Coven
*Attorney, Agent, or Firm*—Roger S. Dybvig

[57] ABSTRACT

A medical electrode assembly which is otherwise free of metal in the area of attachment to a patient so as to be X-ray transparent in such area has a conductive plastic electrode conductor with a silver plated and chlorided coating of a thickness between 0.02 and 0.08 mil. The assembly also has a lead wire formed from an elongate cable having carbon fibers in a low density polymeric jacket and a conductive plastic connector having an opening for gripping a stud formed by the conductive plastic electrode conductor.

29 Claims, 6 Drawing Figures

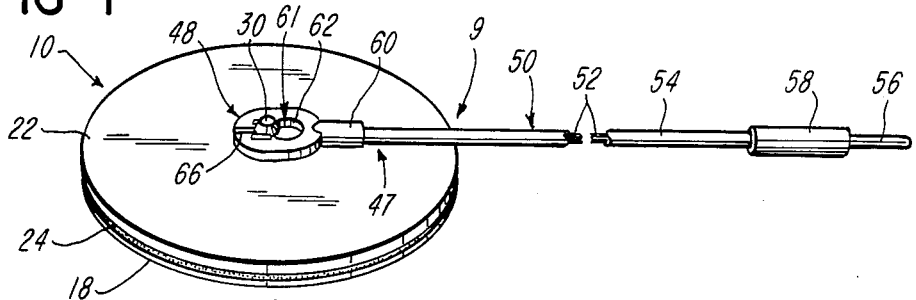
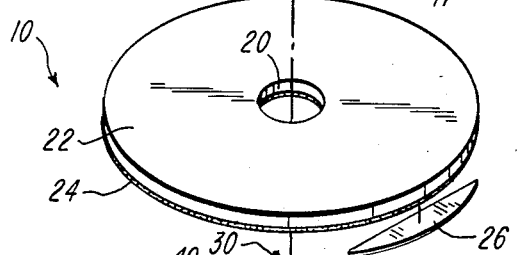
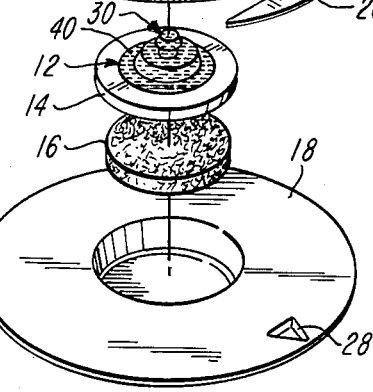
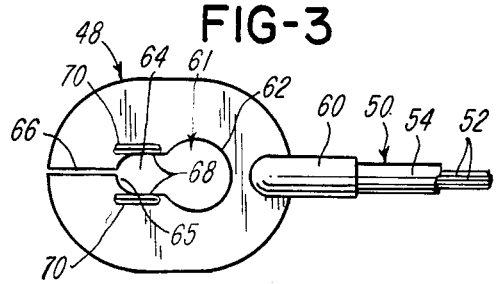
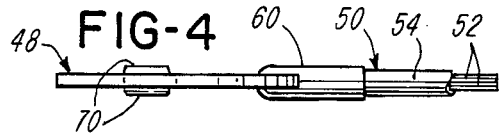
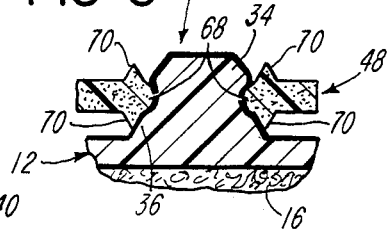
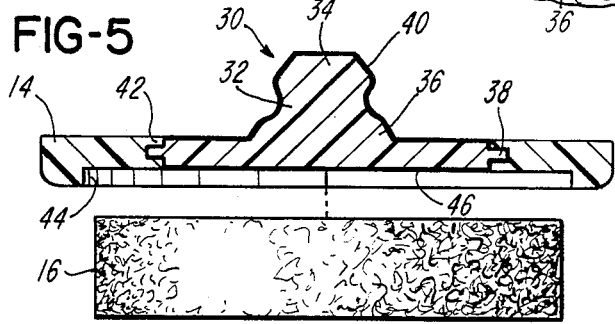

X-RAY TRANSPARENT MEDICAL ELECTRODES AND LEAD WIRES AND ASSEMBLIES THEREOF

SUMMARY OF THE INVENTION

This invention relates to x-ray transparent medical electrodes and lead wires, and in particular to disposable electrodes and reusable lead wires which can be connected together to form an x-ray transparent assembly suitable for transmitting electrical signals between the skin of a patient and peripheral equipment for monitoring biological signals derived therefrom. The medical electrodes and lead wires of this invention are intended to be used for a wide variety of special studies or procedures, such as heart catheterization or angioplasty procedures, wherein x-ray transparency is needed. They are also intended for use in procedures such as nuclear magnetic resonance (NMR) wherein minimal amounts of metal in an electrode can be tolerated. As will become apparent, however, the medical electrodes and lead wires of this invention may be used either with one another or with other devices in other monitoring applications or for other purposes, such as for applying stimulation signals to the skin of a patient.

For purposes of this description and the claims that follow, a device is deemed "x-ray transparent" if it is transparent to x-rays of an intensity used for high resolution cinefluorography of human patients. A lead wire is deemed to be x-ray transparent if it is x-ray transparent at its end, termed the "proximal end" herein, which is connected to the electrode, and is x-ray transparent throughout its cable length notwithstanding the fact that it may have a metallic connector at its opposite end, termed the "distal end" herein, which metallic connector would not be x-ray transparent. To be considered x-ray transparent, the lead wire must also be x-ray transparent over a sufficient length that its distal end can be located entirely outside the area undergoing x-ray examination when its proximal end is connected to an electrode located in the area undergoing examination.

There is a continuing need for x-ray transparent medical electrode assemblies which are of high quality in the sense that they will, when connected to external monitoring equipment, reliably and continuously provide accurate traces of a heart wave with minimal noise or artifacts, and it is an object of this invention to provide such an electrode assembly.

For purposes of convenience and safety, the assembly should include an electrode which is disposable in the sense that it is so inexpensive that it is practical to discard the electrode after only one use. Accordingly, another object of this invention is to provide an inexpensive, high quality, x-ray transparent, medical electrode.

Also for convenience, and to minimize costs, the assembly preferably includes a reusable lead wire, and it is a further object of this invention to provide an improved, reusable, x-ray transparent lead wire. A related object of this invention is to provide a reusable lead wire that is sufficiently rugged that its ability to function properly will not be impaired by ordinary handling and that includes an x-ray transparent cable that is highly flexible and durable so that it can be reused many times.

For optimum diagnostic representation of a heart wave, several monitoring electrodes are adhered to the chest of a patient, each electrode placement revealing a different aspect of the wave. When using such a technique during a procedure in which the area around the heart is undergoing examination by x-ray, it is extremely important that the monitoring electrodes and their lead wires within the x-ray field are x-ray transparent. There are some procedures, particularly heart catheterization and angioplasty, during which defibrillation procedures may be needed in which short bursts of very high electical energy, on the order of 400 or 500 watts per second, are applied one or more times to the patients chest using paddle-shaped electrodes. During defibrillation, a portion of the applied energy will dissipate through monitoring electrodes applied to the patient, especially those in the chest area. Electrodes may be damaged as a result of defibrillation in a mechanical sense in that parts may become overheated and melt or burned as a result of arcing, and also in an electrical sense in that electrical discontinuities may be created. Accordingly, although medical electrodes used for monitoring purposes are primarily used to transmit millivolt level biological signals, it is desirable that x-ray transparent electrodes are both electrically and mechanically uncompromised by the application thereto of high energy pulses resulting from defibrillation procedures so that reliable traces of heart waves will continue to be obtained after the application of defibrillation pulses is terminated.

It is, therefore, another object of this invention to provide an electrode which is x-ray transparent and which will continue to function reliably following the application of defibrillation pulses in the area of the patient's body to which the electrodes are adhered.

Still another object of this invention is to provide an inexpensive, high quality medical electrode assembly having a reusable lead wire and a disposable electrode that will reliably continue to function after application of defibrillation pulses to a patient in the area of the patient's body to which the electrode is adhered.

In accordance with this invention, in order to preserve X-ray transparency in an electrode assembly equipped to carry high currents, an exceptionally thin layer of substantially pure silver is plated onto a low-profile, electrically conductive plastic electrode conductor which is free of metal except for the silver plating and is capable of handling the current-carrying requirements imposed on the electrode. The electrode conductor is provided on one portion thereof with a stud coated by the plating for connection to peripheral equipment and is provided on another portion thereof with a surface coated by the plating, which surface is to be bridged to the skin or tissue of a patient. Even plastic parts, if thick enough, are x-ray visible. Accordingly, the electrode conductor of this invention has a low profile so as to have maximal x-ray transparency. The connection of the stud to peripheral equipment is accomplished by means of a lead wire having a thin, plate-like, conductive plastic connector which tightly grips the silver-plated stud when the connection is accomplished. The combined features of the thin silver plating and the tight engagement between the conductive plastic members minimize contact resistance between the electrode and the lead wire to allow the passage therebetween of high current pulses such as those caused by defibrillation without harm to the electrode assembly. The lead wire also includes an X-ray transparent carbon filament cable for attachment to remote monitoring equipment. The x-ray transparency of the medical electrode assembly is such that the assembly, even though having a relatively high current capability, will not shadow or otherwise reveal itself in X-ray photographs.

Another object of this invention is to provide an improved electrode assembly that may be used for heart catheterization and other special studies procedures including an electrode conductor which is constructed for attachment to conventional snap-fastener lead wires and including a detachable, reusable lead wire. Accordingly, specially constructed lead wires of this invention need be used only in an operating room or other area when X-ray transparency is required and, when the patient is removed to other areas, the electrodes of this invention are left on the patient and conventional lead wires may thereafter be attached to the same electrodes. Conversely, the lead wire is preferably so constructed that it may, if desired, be used with conventional electrodes having snap-fastener studs.

Other objects and advantages will become apparent from the following description and the drawings.

BRIEF DESCRIPTION OF THE DRAWINGS

FIG. 1 is a perspective illustration of the electrode assembly of the present invention with a central portion having been broken away.

FIG. 2 is an exploded perspective illustration of the electrode assembly of FIG. 1 with a portion of a lead wire broken away.

FIG. 3 is an enlarged plan illustration of a connector included in the invention with a portion of a lead wire broken away.

FIG. 4 is a side elevation view of the connector with a portion of the lead wire broken away.

FIG. 5 is an enlarged, exploded sectional illustration of a portion of a medical electrode included in the present invention.

FIG. 6 is a sectional illustration, on the same scale as FIG. 5, of a portion of the electrode assembly of FIG. 1.

DETAILED DESCRIPTION

Referring to the drawings in greater detail, the reference number 9 identifies an x-ray transparent medical electrode assembly in its entirety. The electrode assembly 9 includes an x-ray transparent medical electrode 10, the basic components of which, as it appears in FIGS. 1 and 2, comprise a thin-walled, discoidal, x-ray transparent, electrically conductive, plastic electrode conductor 12 which cooperates with a surrounding, thin-walled, non-conductive, x-ray transparent frame or annulus 14 to form a low-profile cup for receiving a discoidal electrolyte matrix which may comprise an electrolyte-loaded sponge 16. In use, the sponge 16 is contacted to the skin or tissue of a patient for relaying electrical signals between the patient's skin or tissue and the electrode conductor 12. When the electrode assembly 9 is stored, the electrolyte-loaded sponge 16 is protected by a protective cover 18.

The electrode conductor 12 is aligned on a common center axis with an aperture 20 located in a thin-walled, x-ray transparent, foam plastic annulus or body 22 covered on its underside, as it appears in FIG. 2, with a layer of a suitable pressure sensitive adhesive 24.

The pressure-sensitive adhesive 24 is covered along a peripheral section thereof by a suitably shaped finger tab 26 to facilitate removal of the foam plastic body 22 from the protective cover 18 when the electrode is to be used. The protective cover 18 has an embossed arrow 28 to indicate the location of the finger tab 26.

The electrode conductor 12 is shaped to have a generally conical stud 30 sized to enter the aperture 20. Stud 30 has an annular groove forming a narrowed neck 32 therein dividing the stud 30 into a head portion 34 and a base portion 36. The head portion 34 and the neck 32 are shaped and sized for connection to conventional snap-fastener lead wire connectors (not shown).

The electrode conductor 12 comprises a moldable plastic matrix, such as an ethylene vinyl acetate copolymer, which is rendered electrically conductive by the inclusion in the plastic of a dispersion of conductive carbon granules or flakes. As best appears in FIG. 5, the electrode conductor 12 is molded as a one-piece body having a peripherally extending annular tongue 38.

FIG. 5 shows the electrode conductor 12 after it has been insert-molded into an electrically non-conductive plastic frame or annulus 14. However, in accordance with this invention, before such insert-molding, the entire body 12 is covered by a thin coating 40 of pure silver. This layer 40 is preferably formed by plating and then chloriding operations. Silver plated and chlorided plastic parts such as may form the electrode conductor 12 may be obtained from Plating Innovations, Inc., Fitchburg, Mass., 01420. The layer 40 is unique in that, for X-ray transparency, the plating thickness before chloriding is between 0.02 mil and 0.08 mil. This plating thickness is insufficient to insure that, after chloriding, handling and manufacturing operations subsequent to plating, the silver coating 40 will form a continuous conductive metal layer that would provide an electrical path between the stud 30 and the base of the electrode conductor 12 facing the patient's skin. Rather, the conductivity of the conductive plastic material forming the electrode conductor 12 is relied upon to transmit signals from the bottom to the top of the electrode conductor 12.

One function of the silver layer 40 is to provide a galvanically active surface which can efficiently receive electrical signals by way of an electrolyte as taught in U.S. Pat. No. 3,976,055, granted to Monter et al. on Aug. 24, 1976. Thus, the conductive plastic electrode conductor 12, together with the silver layer 40 and the electrolyte-loaded sponge 16, are suitable for the transmission of electrical signals between the electrode conductor 12 and the skin or tissue of a patient engaged by the sponge 16. The layer 40 also provides for a low impedance connection to peripheral equipment as will be discussed below.

After formation of the layer 40, the insert-molding of the electrode conductor 12 is completed and it will be noted that the insert-molding allowed the plastic of the annulus 14 to form a groove 42 receiving the tongue 38. Also, following the insert-molding, the annulus 14 cooperates with the bottom surface 46 of the electrode conductor 12 to form a cup 44. For accomplishing this molding procedure, care is taken not to damage the very thin plating which coats the bottom surface 46. The cup 44 is sized to receive the electrolyte-loaded sponge 16. The sponge 16 is ultrasonically welded to the plastic annulus 14 by conventional ultrasonic welding techniques, with care being taken to cause the ultrasonic welding to occur only on the annulus 14 and remotely from the silvered plastic electrode conductor 12.

The electrode assembly 9 of this invention further includes an x-ray transparent lead wire, generally designated 47, to relay signals from the skin of a patient to peripheral monitoring equipment or, in the alternative, to deliver signals from peripheral equipment to the skin of the patient. Such lead wire 47 comprises an x-ray transparent, conductive plastic connector 48 in the form of a thin-walled plate and an associated electrically conductive but non-metallic and x-ray transparent, elongate cable 50. Cable 50 comprises a bundle of carbon filaments 52 surrounded by a jacket 54 which is preferably an extrusion grade polyurethane polymer because of its low density and consequently low X-ray absorptivity. Other low density polymers may also be suitable. Jacketed carbon filament wires useful in this invention may be obtained from Polimotor Research, Inc., 17-50 River Road, Fair Lawn, N.J. 07410, and, it is believed, from other sources. Such fibers may be produced in various ways. Graphitized polyacrylonitrile (PAN) fibers, such as described in U.S. Pat. No. 4,369,423, to Holtzberg, granted Jan. 18, 1983, are presently preferred because such fibers in a urethane jacket have excellent conductivity and cables from which they are made are quite flexible and durable.

The distal end of the cable 50 is crimped in the body of a metal pin connector 56 which is retained in a plastic sleeve 58. Cable 50 is sufficiently long, 30 inches being exemplary, that the pin connector 56 can be connected to peripheral equipment that is remote from the area of the patient undergoing x-ray examination.

The proximal end of the cable 50 is insert-molded into engagement with the connector 48 at the time the connector 48 is molded to shape. The connector 48 comprises preferably a nylon plastic matrix which is loaded with carbon fibers. At the time the connector 48 is molded, the proximal end of the cable 50, which has been trimmed to expose the proximal ends of the carbon filaments 52, is insert-molded into the plastic of the connector 48 as a socket 60 is formed about the ends of the filaments 52.

As apparent in FIGS. 3 and 4, the connector 48 protrudes symmetrically to the left of the socket 60 and is of a generally oval shape. Formed within the interior of the connector 48 is a keyhole-shaped opening 61 having a larger, circular end 62 and a narrower key-slot 64 having a semicircular end 65. Communicating from the key-slot end 65 to the outside wall of the connector 48 most remote from the socket 60 is a slit 66. The key-slot 64 has sidewalls 68 spaced apart such that the key-slot 64 is slightly narrower than the diameter of the stud neck 32. Circular slot end 62 is sufficiently large to receive the stud 30. With the stud 30 located in the circular opening part 62, the stud 30 may be advanced relatively laterally away from the socket 60 so that the stud neck 32 is forced to wedge between the slot side walls 68. This wedging action results because the diameter of the neck 32 slightly exceeds the width of the slot 64. To avoid accidental disengagement of the stud 30 from the key-slot 64, the key-slot end 65 is slightly larger than the rest of the slot 64, although still smaller than the diameter of the neck 32. Accordingly, when the connector 48 is mounted on the stud 30, the neck 32 will be lodged securely in the key-slot end and the slot side walls 68 will resist removal of the stud 30.

As the neck 32 is wedged into the key-slot 64, the slit 66 opens to relieve the stresses being generated by the misfit between the neck 32 and the key-slot 64. While the stresses being generated by the wedging of the neck 32 into the key-slot 64 are thus relieved, there is a resilient, squeezing pressure applied by the key-slot side walls 68 against the neck 32 resulting from a resistance of the body of the connector 48 to change its shape.

Accordingly, the connector 48 grips the neck 32 so that there is a firm mechanical connection and a good, low-impedance, electrical connection therebetween. It is believed that the squeezing pressure causes the side walls 68 to scrape the silver plating 40 as the lead wire is being connected to the stud 30 which scraping may remove oxides that may have formed on the neck 32 to further enhance the transmission of electrical signals between the connector 48 and the silver plating 40 on the neck 32.

To increase the contact area between the connector 48 and the stud 30, and thus lower the contact resistance therebetween, the connector 48 may be provided with tapered flanges 70 adjacent the key-slot side walls 68 shaped, as shown in FIG. 6, to snugly engage the outer wall of the stud base portion 36. The flanges 70 extend both upwardly and downwardly from the key-slot side walls 68 so that the connector 48 may be attached to the stud 30 without concern with which side of the connector 48 is facing upwardly. Also, in FIG. 6, it may be observed that the key-slot side walls 68 are formed to conform to the shape of the stud neck 32 to provide good contact therebetween.

In the construction of the electrode above described, the plastic electrode conductor 12 is inserted into the aperture 20 of the foam plastic body 22 with the adhesive of the layer 24 engaging the exposed upper surfaces of the electrode conductor 12 and the annulus 14 as they appear in FIG. 2. With the electrolyte-loaded sponge 16 having been ultrasonically welded to the annulus 14 and the electrode conductor 12 having been insert-molded within the annulus 14, the sponge 16, the electrode conductor 12, and the foam plastic body 22 are joined together in a one-piece construction. During storage of the electrode assembly, the sponge 16, as well as the adhesive layer 24, are protected by the protective cover 18.

In preparation for use of the electrode assembly, the protective cover 18 is peeled away from the adhesive layer 24 underlying the foam plastic body 22 with the adhesive engaged by the upper surfaces of the electrode conductor 12 and the annulus 14 causing the electrode conductor 12, the annulus 14, and the sponge 16 to follow the foam plastic body 22. This portion of the electrode assembly may then be attached to the skin of a patient by the adhesive layer 24.

Connection to the peripheral equipment is then effected by placing the connector 48 onto the stud 30 and moving the connector 48 laterally to wedge the neck 32 into the key-slot 64, thus establishing an electrical path from the electrolyte-loaded sponge 16 through the conductive plastic electrode conductor 12, through the connector 48, through the carbon filaments 52, and ultimately through the pin connector 56.

Should the electrode assembly have been applied to the patient for monitoring purposes, the signals transmitted between the patient's skin and any peripheral equipment engaged by the pin connector 56 will be in generally the millivolt range. Should the monitoring conditions warrant the accomplishment of a special procedure such as defibrillation, this may affect the electrode assembly being described because the defibrillation power may find a ground through the electrode assembly described. This will increase the current flow through the electrode assembly substantially beyond the current range experienced during ordinary monitoring and this substantially higher current level will bring into play the silver plating 40 present on the stud 30 because the plating has been found sufficient to keep the contact resistance to an acceptably low level so that the electrode assembly remains operable. Without the plating, arcing could occur at the interface between a conductive plastic stud and a conductive plastic connector which could result in an inability of the electrode assembly to function due to melting or burning of the conductive plastic parts at their interface. Arcing could also create a fire hazard in the operating room in which such an electrode assembly were used.

One of the particular advantages of the invention of the present invention is that it is X-ray transparent in all currently-practiced special studies medical X-ray procedures. To achieve this degree of X-ray transparency, it is important that the medical electrode assembly be produced from thin, low-profile parts that are free of metal except as noted above. The silver plating 40 constitutes the only metal included in the X-ray assembly except for the pin connector 56 which is at the distal end of the lead wire 47 and remote from the site of attachment of the electrode assembly 9 to the skin. The silver plating 40 is acceptable only because it does not exceed 0.08 mils in thickness. Regarding the cable 50, it is important that the carbon filaments 52 are non-metallic and it is also important that the surrounding jacket 54 comprises a low density polymer such as a polyurethane polymer. It is also preferable that the connector 48 be free of metal and thus comprises a plastic such as nylon loaded with graphite fibers. It is also desirable, as taught in said Monter et al U.S. Pat. No. 3,976,055, that the conductive plastic electrode conductor 12 comprise a plastic loaded with a galvanically inactive conductor such as carbon which can be bridged to the electrolyte loaded in the sponge 16 by the thin coating or plating of galvanically active silver underlying the bottom surface 46 of the electrode conductor 12. This construction provides an optimal, non-polarizing connection between the sponge 16 and the silver plating 40. Because of the minimal amount of metal embodied near the site of application to the skin in the electrode assemblies of this invention, those familiar with the art will recognize that this invention may also advantageously be used in connection with nuclear magnetic resonance (NMR) and CAT scan procedures.

The conductive plastic electrode conductor 12 and the conductive plastic connector 48 could be made from polymeric materials other than those recommended above. It may also be possible to use substantially pure metals other than silver, such as nickel or zinc, for the plating material provided that the proper electrolyte is used, as is well known to those familiar with the art. Silver is preferred because of its high conductivity and its resistance to polarization. Silver also is well recognized as the preferred metallic conductor for high quality, reliable, pre-gelled electrodes.

The type of plastic and the metal used may affect the dimensions of the parts. As an example, a satisfactory electrode assembly in accordance with this invention has been constructed which has a connector 48 made from nylon which is 0.050 inch thick, a socket 60 which is 0.125 inch in diameter, and flanges 70 extending approximately 0.030 inch each direction. The diameter of the circular part 62 of its opening 61 is 0.228 inch and the key-slot 64 has a width of about 0.134 inch, increased to about 0.138 inch at its end most remote from the circular part 62, for use with a stud neck 32 having a diameter of 0.140 inch. The slit 66 is approximately 0.020 inch minimum. The electrode conductor 12, made from EVA with carbon, and having a silver plating, before chloriding of approximately 0.05 mils, is 0.050 inch thick and the stud 30 projects 0.140 inch upwardly therefrom, the stud 30 having a maximum diameter at its base of 0.230 inch and a minimum diameter at its top of 0.100 inch. Annulus 14 has an outer diameter of 0.938 inch, an inner diameter of 0.545 inch, and a maximum thickness at its rim of 0.220 inch.

In use, it is contemplated that a number of electrodes of this invention will be adhered to the skin of a patient about to undergo a heart catheterization, angioplasty, or other special studies procedure and that the monitoring equipment in the operating room or other area in which the procedure is to take place will be connected to the electrodes using the lead wires of this invention. After completion of the procedure, the lead wires are preferably disconnected from the electrodes so that they may be re-used in the special studies area. The patient is normally removed to another area where monitoring equipment may be attached to the electrodes by lead wires having conventional snap-fastener connectors. Thus, substantial economies are achieved because the electrodes 10 may be used with conventional lead wires for routine monitoring and also because the lead wires 47 may be used many times.

It may also be observed that the connector 48 may be connected to a conventional snap fastener stud so that it may be used with electrodes having such studs.

Although the preferred embodiment of this invention has been described, it will be understood that various changes may be made within the scope of the appended claims.

Having thus described our invention, we claim:

1. In an x-ray transparent medical electrode assembly of the type comprising a conductor, means for bridging the conductor to human tissue, and connector means detachably connected to said conductor for connecting said conductor to peripheral equipment, the improvement wherein said conductor comprises a conductive plastic body that includes a stud having a thin metal coating on its outer surface, wherein said connector means comprises a conductive plastic body having an opening extending therethrough for receiving said stud, and wherein said body has surface portions defining marginal portions of said openings that resiliently grip said outer surface of said stud when said connector means is connected to said conductor.

2. The medical electrode assembly of claim 1 wherein said body of said connector means conprises a polymeric matrix filled with carbon.

3. The medical electrode assembly of claim 1 wherein said connector means further comprises a cable comprising a bundle of carbon filaments contacting and extending into said body of said connector means.

4. The medical electrode assembly of claim 3 wherein said cable has a polyurethane jacket surrounding said carbon filaments.

5. The medical electrode assembly of claim 1 wherein said opening has a keyhole shape with a larger part and a smaller part for receiving said stud in said larger part and for slideably accepting said stud in said smaller part and wherein said surface portions of said body resiliently gripping said outer surface of said stud define marginal portions of said smaller part.

6. The medical electrode assembly of claim 5 wherein said conductive plastic body of said connector means further has a slit extending therethrough communicating with said smaller part and opening to the outer margin of said body to enable said side wall portions therof to be spread apart upon insertion of said stud therein.

7. The medical electrode assembly of claim 1 wherein said conductor has a base surface which has a metal coating and wherein said means for bridging the conductor to human tissue comprises an electrolyte engaging said base surface.

8. The medical electrode assembly of claim 7 wherein said body of said conductor comprises a plastic matrix rendered conductive by included carbon and wherein said metal coating on said stud and said metal coating on said base surface comprise a chlorided silver plating on the outer surface of said outer body of said conductor.

9. The medical electrode assembly of claim 8 wherein said silver plating has a thickness before chloriding in the range of 0.02 to 0.08 mils.

10. The medical electrode assembly of claim 1 wherein said conductor is mounted in a surrounding frame of non-conductive plastic and wherein said means for bridging comprises an electrolyte-loaded sponge, peripheral portions of said sponge being affixed to said frame.

11. The medical electrode assembly of claim 10 wherein said conductor has a surrounding tongue lodged within a groove within said frame.

12. The medical electrode assembly of claim 1 wherein said stud has a generally cylindrical shape and has a head portion and a neck portion for connection to a snap-fastener connector.

13. The medical electrode assembly of claim 12 wherein said stud has a base portion below said neck portion, said portion base having a generally conical shape, said marginal portions of said connector are shaped to engage said neck portion, and said connector has flanges adjacent said marginal portions shaped to engage the outer wall of said base portion.

14. An x-ray transparent medical electrode assembly comprising:
a low-profile, x-ray transparent, plastic electrode conductor made conductive by the inclusion of carbon and having a thin metallic coating on surface portions thereof;
an electrolyte engaged with a surface portion of said conductor coated with said thin metallic coating for electrically bridging between said conductor and the skin of a patient;
means connected to said conductor for adhering said conductor and said electrolyte to the skin of a patient;
an x-ray transparent cable;
means connected to one end of said cable for electrical connection to monitoring equipment; and
x-ray transparent means for detachably connecting said cable to said conductor comprising a pair of tightly interfitting, conductive plastic members, including a first conductive plastic member which is integrally fixed to said conductor and a second conductive plastic member which is integrally fixed to said lead wire, one of said members having a chlorided silver coating having a thickness before chloriding in the range of 0.02 to 0.08 mils, so that said pair of members when assembled to one another are x-ray transparent and are electrically and mechanically uncompromised by the application thereto of high energy pulses resulting from defibrillation procedures so that reliable traces of heart waves will continue to be obtained after defibrillation pulses have been applied to a patient to whom the electrode assembly is applied.

15. The medical electrode assembly of claim 14 wherein said first conductive plastic member comprises a stud integral with said conductor and said second conductive plastic member comprises a connector at the other end of said cable having an opening for snugly receiving said stud.

16. The medical electrode assembly of claim 15 wherein said connector comprises a thin-walled plate having marginal portions bounding said opening for resiliently gripping said stud.

17. The medical electrode assembly of claim 16 wherein said opening has a keyhole shape with a larger part and a smaller key-slot part for receiving said stud in its larger part and for slideably accepting said stud in said key-slot part and wherein said marginal portions bounding said opening comprise side wall portions of said key-slot part.

18. The medical electrode assembly of claim 17 wherein said plate further has a slit extending therethrough communicating with said key-slot part and opening to the outer margin of said body to enable said side wall portions to be spread apart upon insertion of said stud therein.

19. The medical electrode assembly of claim 18 wherein the opening of the end of said key-slot part remote from said larger part is slightly larger than the rest of said key-slot part but slightly smaller than the portion of said stud received therein.

20. For use with a medical electrode of the type having a stud, a lead wire comprising an x-ray transparent cable comprising a bundle or carbon filaments in a polymeric jacket, an X-ray transparent connector connected to said filaments, said X-ray transparent connector comprising a thin-walled plate formed from conductive plastic and having an opening for snugly receiving said stud, said plate having marginal portions bounding said opening for resiliently gripping said stud.

21. The medical electrode assembly of claim 20 wherein said opening has a keyhole shape with a larger part and a smaller key-slot part for receiving said stud in its larger part and for slideably accepting said stud in said key-slot part and wherein said marginal portions bounding said opening comprise side wall portions of said key-slot part.

22. The medical electrode assembly of claim 21 wherein said plate further has a slit extending therethrough communicating with said key-slot part and opening to the outer margin of said body to enable said side wall portions to be spread apart upon insertion of said stud therein.

23. The medical electrode assembly of claim 22 wherein the opening of the end of said key-slot part remote from said larger part is slightly larger than the rest of said key-slot part but slightly smaller than the portion of said stud received therein.

24. An x-ray transparent medical electrode assembly comprising:
a low-profile, x-ray transparent, plastic electrode conductor made conductive by the inclusion of carbon and having a thin metallic coating on surface portions thereof;
an electrolyte engaged with a surface portion of said conductor coated with said thin metallic coating for electrically bridging between said conductor and the skin of a patient;

means connected to said conductor for adhering said conductor and said electrolyte to the skin of a patient;

an x-ray transparent cable;

means connected to one end of said cable for electrical connection to monitoring equipment; and x-ray transparent means for detachably connecting said cable to said conductor comprising a pair of tightly interfitting, conductive plastic members, including a first conductive plastic member which is integral with said conductor and a second conductive plastic member which is integral with said lead wire, said first conductive plastic member comprising a stud having a head portion and a neck portion for connection to a snap-fastener connector, said stud further having a base portion below said neck portion, said neck portion having a smaller thickness than said head portion and said base portion, and said second conductive plastic member comprising a thin-walled plate having an opening extending therethrough for receiving said stud, said opening having a larger part for receiving said stud and a smaller part, said plate having relatively movable confronting side walls bounding said smaller part for slideably accepting said neck portion that are mutually spaced apart by a distance less than the thickness of said neck portion and are forced apart upon slideable insertion of said neck portion therebetween so that said side walls firmly grip said neck portion.

25. The medical electrode assembly of claim 24 wherein said base portion of said stud has a generally conical shape and said connector has flanges adjacent said side walls shaped to engage the outer wall of said base portion.

26. The medical electrode assembly of claim 25 wherein said plate has a gap communicatihg with said smaller part and opening to the outer margin of said plate to enable said side wall portions therof to be spread apart upon insertion of said stud therein.

27. The medical electrode assembly of claim 24 wherein said stud has a chlorided silver coating having a thickness before chloriding in the range of 0.02 to 0.08 mils.

28. The medical electrode assembly of claim 24 wherein said x-ray transparent cable comprises a bundle of carbon filaments contacting and extending into said thin-walled plate.

29. The medical electrode assembly of claim 28 wherein said cable has a polyurethane jacket surrounding said carbon filaments.

* * * * *

UNITED STATES PATENT AND TRADEMARK OFFICE
CERTIFICATE OF CORRECTION

PATENT NO. : 4,685,467

DATED : August 11, 1987

INVENTOR(S) : James V. Cartmell, Michael J. Allaire, Larry R. Burcham, Charles T. Patrick, Jr.

It is certified that error appears in the above-identified patent and that said Letters Patent is hereby corrected as shown below:

Column 2, line 9, "patients" should be --patient's--.
Column 7, line 11, delete "of the invention". Column 9, line 33, "portion base" should be --base portion--. Column 10, line 34, "or" should be --of--.

Signed and Sealed this

Thirtieth Day of July, 1991

Attest:

HARRY F. MANBECK, JR.

Attesting Officer

Commissioner of Patents and Trademarks